United States Patent
El-Dweik

(10) Patent No.: US 11,150,244 B2
(45) Date of Patent: Oct. 19, 2021

(54) APPARATUS AND METHOD FOR DETECTING MICROBIAL CONTAMINATION

(71) Applicant: S D Systems, Inc., Columbia, MO (US)

(72) Inventor: Majed El-Dweik, Columbia, MO (US)

(73) Assignee: S D SYSTEMS, INC., Columbia, MO (US)

( * ) Notice: Subject to any disclaimer, the term of this patent is extended or adjusted under 35 U.S.C. 154(b) by 0 days.

(21) Appl. No.: 16/671,022

(22) Filed: Oct. 31, 2019

(65) Prior Publication Data

US 2020/0132687 A1 Apr. 30, 2020

Related U.S. Application Data

(63) Continuation of application No. PCT/US2018/031679, filed on May 8, 2018.

(60) Provisional application No. 62/503,147, filed on May 8, 2017, provisional application No. 62/502,987, filed on May 8, 2017.

(51) Int. Cl.
| | |
|---|---|
| *G01N 33/53* | (2006.01) |
| *G01N 33/569* | (2006.01) |
| *C07K 16/12* | (2006.01) |
| *G01N 33/541* | (2006.01) |
| *G01N 33/543* | (2006.01) |
| *G01N 33/577* | (2006.01) |

(52) U.S. Cl.
CPC ... *G01N 33/56916* (2013.01); *C07K 16/1235* (2013.01); *G01N 33/541* (2013.01); *G01N 33/54326* (2013.01); *G01N 33/54393* (2013.01); *G01N 33/577* (2013.01)

(58) Field of Classification Search
None
See application file for complete search history.

(56) References Cited

U.S. PATENT DOCUMENTS

| | | |
|---|---|---|
| 4,144,452 A | 3/1979 | Harte |
| 5,624,821 A | 4/1997 | Winter et al. |
| 5,648,260 A | 7/1997 | Winter et al. |
| 5,958,706 A | 9/1999 | Matsunaga et al. |
| 6,331,438 B1 | 12/2001 | Aylott et al. |
| 2006/0088895 A1 | 4/2006 | Wanders |
| 2009/0021728 A1 | 1/2009 | Heinz |
| 2014/0093975 A1 | 4/2014 | Wang |
| 2014/0170767 A1* | 6/2014 | Lee .................. G01N 33/54326 436/501 |
| 2015/0153335 A1 | 6/2015 | Hamasaki |
| 2017/0219615 A1 | 8/2017 | Matsumoto |

FOREIGN PATENT DOCUMENTS

| | | |
|---|---|---|
| AU | 2018266138 | 10/2019 |
| CA | 3060696 | 10/2019 |
| CN | 102043053 A | 5/2011 |
| CN | 103913577 A | 7/2014 |
| EP | 18798453.9 | 12/2019 |

OTHER PUBLICATIONS

Meza et al (Scientific and Clinical Applications of Magnetic Carriers. "Application of Magnetic Particles in Immunoassays" 1997, pp. 303-309).*
USP (1102. Immunological Test Methods. Second supplement. (1103) Immunological Test Methods—Enzyme-linked Immunosorbent Assay (ELISA), pp. 5678-5686. Dec. 2012).*
Nishi et al (Sensors 2015, 15, 25831-25867; doi:10.3390/s151025831 ).*
Kabat et al. (1971) "Attempts to locate complementarity determining residues in the variable positions of light and heavy chains," Ann. NY Acad. Sci., 190, pp. 382-391.
Kabat et al. (1991) Sequences of Proteins of Immunological Interest, Fifth Edition. NIH Publication No. 91-3242, 425 pp.
Chothia et al. (1987) "Canonical Structures for the Hypervariable Regions of Immunoglobulins," J. Mol. Biol., 196, pp. 901-917.
Chothia et al. (1989) "Conformations of immunoglobulin hypervariable regions," Nature, 342, pp. 877-883.
Padlan et al. (1995) "Identification of specificity-determining residues in antibodies," FASEB J., 9, pp. 133-139.
MacCallum (1996) "Antibody-antigen Interactions: Contact Analysis and Binding Site Topography," J. Mol. Biol., 262(5), pp. 732-745.
International Search Report and Written Opinion of PCT/US2018/031679 dated Jul. 23, 2018, 10 pp.
U.S. Appl. No. 16/881,729, filed May 22, 2020, Majed El-Dweik.
U.S. Appl. No. 16/881,729, Final Office Action dated Mar. 9, 2021.
U.S. Appl. No. 16/881,729, Non-Final Office Action dated Nov. 25, 2020, 30 pages.
Mu et al. "Nano-Magnetic Immunosensor Based on *Stephylococcus* Protein A and the Amplication Effect of HRP-Conjugated Phage Antibody" Sensors 2015, 15, 3896-3910;doi:10.3390/s150203896 (Year: 2015).
McCafferty et al."Phage Antibodies: filamentous phage displaying antibody variable domains" Nature vol. 348, pp. 552-554 (1990) (Yea: 1990).

(Continued)

*Primary Examiner* — Jennifer E Graser
(74) *Attorney, Agent, or Firm* — Lathrop GPM LLP; Gordon R. Moriarty

(57) ABSTRACT

Provided are novel methods for screening and testing for pathogens in food, water, and bodily fluids using methods that are faster to complete than conventional methods of culturing and plating that require lengthy times in properly equipped labs. The invention utilizes specific, rapid and sensitive optical detection to capture small concentrations of the target bacteria and render them amenable for detection with various specific synthesis binding agents approaches. The technique merges capture and detection steps with quantification unit suitable to provide results in a relatively shorter time current detection methods.

20 Claims, 10 Drawing Sheets

(56) References Cited

OTHER PUBLICATIONS

Sunwoo H H et al., Detection of *Escherichia coli* 0157:h7 Using Chicken Immunoglobulin Y, Immunology Letters, Elsevier BV, NL, vol. 106, No. 2, Aug. 15, 2006.

Naiyana Gujral et al., Sensitive Double Antibody Sandwich ELISA for the Quantification of Phosvitin, Food and Agricultural Immunology, vol. 28, No. 5, Apr. 14, 2017.

Daniel Horak et al., Abstract E-Polymers, vol. 5, No. 1, Dec. 1, 2005.

Du Plessis D H et al., The Use of Chicken IgY in a Double Antibody Sandwich ELISA for Detecting African Horsesickness Virus, Onderstepoort Journal of Veterinary Research, Pretoria: Agricultural Research Council, ZA, vol. 66, No. 1, Mar. 1, 1999.

Haiyan Xue et al., Rapid Immunochromatographic Assay for *Escherichia coli* 0157: H7 in Bovine Milk Using IgY Labeled by $Fe_3O_4$Au Composite Nanoparticles, Food Science and Technology Research, vol. 22, No. 1, Jan. 1, 2016.

Salma Teimoori et al., Chicken IgY-based Coproantigen Capture ELISA for Diagnosis of Human Opisthorchiasis, Parasitology International, vol. 66, No. 4, Apr. 26, 2016.

Ji-Long Shen et al., Evaluation of an IgY-Based Immunomagnetic Enzyme-Linked Immunosorbent Assay System for Detection of Circulating Schistosoma Japonicum Antigen in Serum Samples from Patients in China, American Journal of Tropical Medicine and Hygiene, vol. 85, No. 6, Dec. 1, 2011.

Chu Pei-Tzu et al., Sensitive Detection and Quantification of Gliadin Contamination in Gluten-Free Food with Immunomagnetic Beads Based Liposomal Fluorescence Immunoassay, Analytica Chimic Acta, Elsevier, Amsterdam, NL, vol. 787, May 27, 2013.

Jason S. Kim et al., Multiplexed Magnetic Microsphere Immunoassays for Detection of Pathogens in Foods, Sensing and Instrumentation for Food Quality and Safety, vol. 4, No. 2, May 4, 2010.

Ratthaphol Charlermroj et al., Multiplex Detection of Plant Pathogens Using a Microsphere Immunoassay Technology, Plos One, vol. 8, No. 4, Apr. 26, 2013.

Jin Wanchun et al., Application of IgY to 1-7 Sandwich Enzyme-Linked Immunosorbent Assays, Lateral Flow Devices, and Immunopillar Chips for Detecting *Staphylococcal* Enterotoxins in Milk and Dairy Products, Journal of Microbiological Methods, Elsevier, Amsterdam, NL, vol. 92, No. 3, Jan. 11, 2013.

EP Application No. 18798453.9, Extended European Search Report dated Apr. 30, 2021, 15 pages.

\* cited by examiner

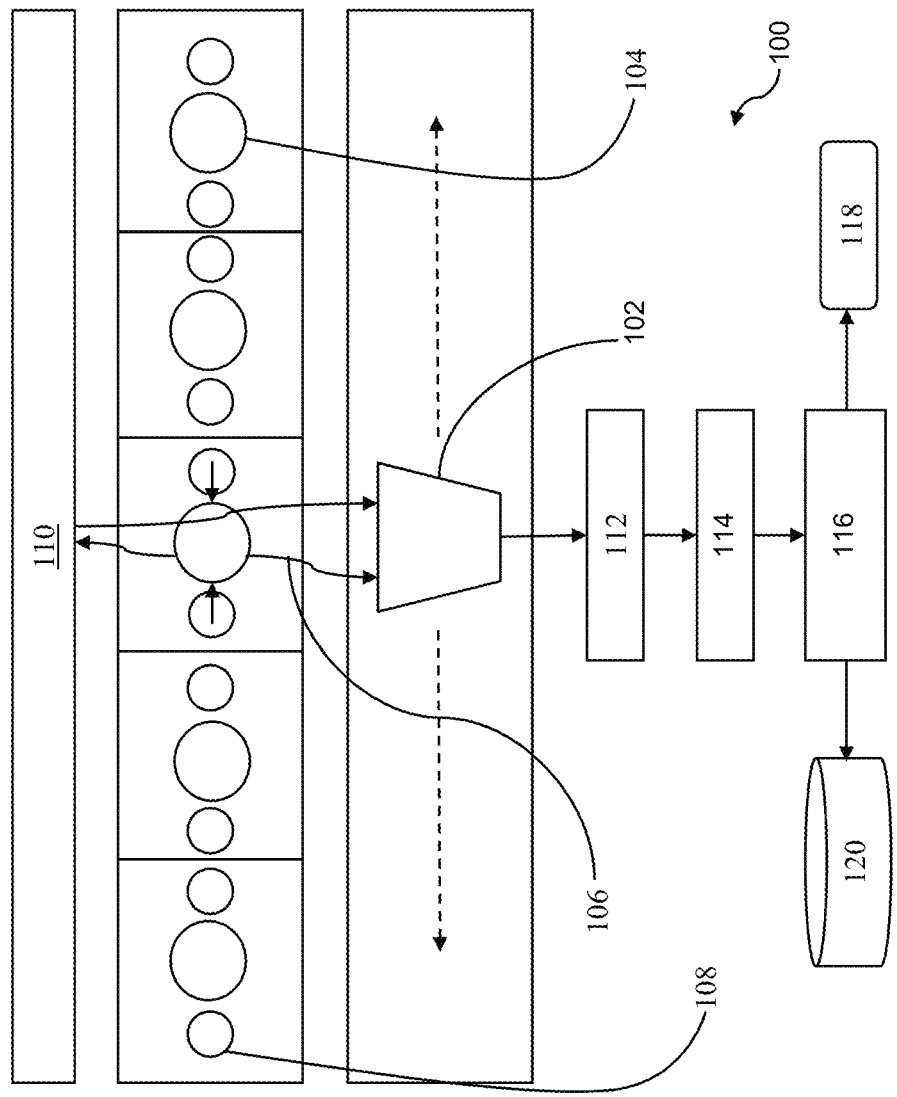

APPARATUS AND METHOD FOR DETECTING MICROBIAL CONTAMINATION

RELATED APPLICATIONS

This application is a continuation of PCT/US2018/031679, filed May 8, 2018, which claims priority to U.S. Ser. No. 62/502,987, filed May 8, 2017, and U.S. Ser. No. 62/503,147, filed May 8, 2017. The contents of these applications are incorporated herein by reference in their entireties.

FIELD

The present invention relates to methods and apparatus for detecting microorganisms, including infectious bacteria, in substances such as food, water, and bodily fluids.

BACKGROUND

Although some strains of microbes, such as bacteria, are beneficial for living beings, there are pathogenic strains of microbes that nevertheless cause disease in humans. For example, one of the major routes by which pathogenic bacteria infect the human body is via ingestion of contaminated water or food. Foodborne pathogenic bacteria are a major cause of morbidity and mortality in humans. Due to the huge impact of foodborne bacterial morbidity on the community, it is important to ensure that consumers receive water and food materials free of potential contamination by pathogens. Therefore, testing and surveying water and food products for potential foodborne pathogens are standard procedures in many industries.

However, most of the conventional methods for testing water and food samples require relatively long times and may also require additional time for sample enrichment to meet the minimal detectible level for the tests.

SUMMARY

The invention is based in part on the discovery of a fast and accurate method for screening for microbial pathogens in food products, water and bodily fluids.

In one aspect, the disclosure provides a method of detecting a food-borne pathogen. The method comprises mixing a solution comprising a sample suspected of containing the food-borne pathogen and a capture antibody, which specifically binds to an antigen on the food-borne pathogen, in conditions sufficient to form a first complex between the pathogen and the capture antibody when the food-borne pathogen is present at a concentration as low as one viable cell per 125 g for up to 425 g of the sample, and wherein the capture antibody is linked to an immobilization moiety. Unbound capture antibody is separated from the first complex, and a detector antibody is added. The detector antibody is linked to a detection moiety and specifically binds at a distinct site on the same antigen to which the capture antibody specifically binds. The detector antibody does not comprise an IgG Fc region. The detector antibody is added under conditions sufficient to form a second complex between the first complex and the detector antibody. Unbound detector antibody is separated from the second complex, and the detection moiety is detected on the second complex, thereby detecting the food-borne pathogen.

In some embodiments, the method further comprises culturing the solution comprising a sample suspected of containing the food-borne pathogen under conditions sufficient to allow for growth of the pathogen prior to mixing the solution with the capture antibody.

In some embodiments, the pathogen is an infectious agent.

In some embodiments, the pathogen is a bacteria, e.g., an *E. coli* or *Salmonella* spp.

In some embodiments, the bacteria is an *E. coli* O157:H7 strain.

In some embodiments, the capture antibody is an IgG antibody.

In some embodiments, the immobilization moiety is a magnetic particle.

In some embodiments, the magnetic particle has an average diameter of between 20 nm and 165 µm.

In some embodiments, the magnetic particle is coated with a protein that binds an immunoglobulin protein, e.g., the protein is Protein A which can include, recombinant Protein A.

In some embodiments, the detector antibody is an IgY antibody.

In some embodiments, the detection moiety is horse radish peroxidase (HRP).

In some embodiments, the detection moiety is a fluorescent dye, e.g., a fluorescent dye with an excitation wavelength between 450 nm to 700 nm.

In another aspect, the disclosure features a method of a detecting an *E. coli* O157:H7 strain. The method comprises mixing a solution comprising a sample suspected of containing *E. coli* O157:H7 and a capture antibody, which specifically binds to an antigen on *E. coli* O157:H7, in conditions sufficient to form a first complex between *E. coli* O157:H7 and the capture antibody when the *E. coli* O157:H7 pathogen is present at a concentration as low as one viable cell per 125 g of the sample. The capture antibody is linked to a magnetic particle with a diameter from 20 nm to 165 µm and the magnetic particle is coated with Protein A. Unbound capture antibody is separated from the first complex. An IgY detector antibody, which specifically binds at a distinct site on the same *E. coli* O157:H7 antigen to which the capture antibody specifically binds, is added under conditions sufficient to form a second complex between the first complex and the detector antibody, and unbound detector antibody is separated from the second complex; The second complex is detected, thereby detecting *E. coli* O157:H7.

In some embodiments, the method further comprises culturing the solution comprising a sample suspected of containing the *E. coli* O157:H7 under conditions sufficient to allow for growth of the *E. coli* O157:H7 prior to mixing the solution with the capture antibody.

In a further aspect, the disclosure features a method of detecting an antigen by mixing a solution comprising a sample suspected of containing the antigen and a capture antibody, which specifically binds to the antigen, in conditions sufficient to form a first complex between the antigen and capture antibody when the antigen is present in the sample at a concentration as low as 1 cell/100 ml, wherein the capture antibody is linked to an immobilization moiety; and separating unbound capture antibody from the first complex. A detector antibody linked to a detector moiety is added. The detector antibody specifically binds at a distinct site on the antigen to which the capture antibody specifically binds. The detector antibody is added under conditions sufficient to form a second complex between the first complex and the detector antibody. Unbound detector antibody is separated from the second complex; and the second complex is detected, thereby detecting the antigen.

In a still further aspect, the disclosure features an optical instrument for biological analysis. The instrument comprises a light source emitting electromagnetic radiation to a sample holder controlled by magnetic field disposed on a movable platform, the sample holder configured to receive a plurality of biological samples; one or more optical detectors configured to receive an emission from the biological samples; and a digital decoder in communication with the optical detector that converts the emission to a detectable signal.

In another aspect, the disclosure features an optical instrument for biological analysis. The optical instrument comprises an array of sample container receiving positions; at least one light source adjacent to each sample container receiving position for providing illumination at a first wavelength range and in a first illumination direction through a respective sample container disposed within the sample container receiving position; and a photodetector disposed adjacent each sample container receiving position for selectively detecting light radiated from the respective sample container in response to illumination from the respective at least one light source, the detected light corresponding to a concentration of an antigen concentration within the respective sample container.

In another aspect, the disclosure provides an apparatus comprising a capture antibody linked to an immobilization moiety, wherein the immobilization moiety is a magnetic particle with a diameter from 20 nm to 165 μm and wherein the magnetic particle is coated with protein; and a detector antibody linked to a detection moiety, wherein the detector antibody does not include an IgG Fc region, and wherein the capture antibody and detector antibody specifically bind to the same antigen at distinct sites.

The optical detection method and apparatus combines microbial capture and detection in as little as one step. Moreover, the methods can be performed at between 20 and 60 degrees Celsius. The results can be conveniently provided as quantified in an optical detection platform, which allows for the detection to be performed on site with minimal technical requirements. Moreover, using different primary binding agents in the platform allow the platform to be potentially utilized as an array for testing a constellation of various potential bacterial contaminants of water and food on the scene.

The advantages provided by the methods and apparatuses disclosed herein include combining bacterial capture and quantitative testing using immunomagnetic particles and an optical detection platform. The relatively short steps required by the methods permit the test to be conducted at room temperature and the results are quantified in a portable optical detection platform. These features allow for the detection to be performed on site with minimal technical expertise and requirements to conduct the test The micro-spherical optical platform is additionally designed to minimize or prevent a high false negative rate. This system can be optimized to detect low counts of viable cells, i.e., in the range 0.008 to 0.078 cells per 125 g and 0.002 to 0.02 cells per 450 g meat sample. This automated multi channels detection system will reduce the detection time to 30 minutes after a reduced enrichment time to 8 hours.

Those skilled in the art will be aware that the invention described herein is subject to variations and modifications other than those specifically described. It is to be understood that the invention described herein includes all such variations and modifications. The invention also includes all such steps, features, compositions and compounds referred to or indicated in this specification, individually or collectively, and any and all combinations of any two or more of the steps or features.

BRIEF DESCRIPTION OF THE FIGURES

The following figures form part of the present specification and are included to further illustrate aspects of the present invention.

FIG. 10 is a schematic view of a photodetector system for use in detecting target antigens.

DETAILED DESCRIPTION

Pathogenic microbes, such as types of *E. coli*, are the cause of many epidemic outbreaks of morbidity and mortality all-over the world. Pathogenic *E. coli* can cause a wide spectrum of GI diseases that can be fatal in untreated and/or undiagnosed patients. Virulent *E. coli* impose a public health concern because of their low infectious doses and easy transmission through food and water. *E. coli* infection can cause intestinal and extra-intestinal manifestations. *E. coli* O157:H7, for instance, is one of the most important enterohemorrhagic *E. coli* (EHEC) strains that causes diarrhea and hemorrhagic colitis, which may proceed to a life-threatening hemolytic uremic syndrome (HUS). *E. coli* O157:H7 infection, in the United States, is estimated to be approximately 75,000 cases annually.

In certain embodiments, the methods and apparatuses disclosed herein use optical platform separation (OPS), which is also known as immunomagnetic separation (IMS) to isolate and purify specific molecules from a fluid known to or suspected of containing a pathogen. OPS uses paramagnetic particles coated with antibodies (Abs) to specifically isolate target antigens. By applying a magnetic field, the particles with the captured antigen are attracted to the magnet, which allows the rest of the liquid solution to be decanted.

Figure 1:
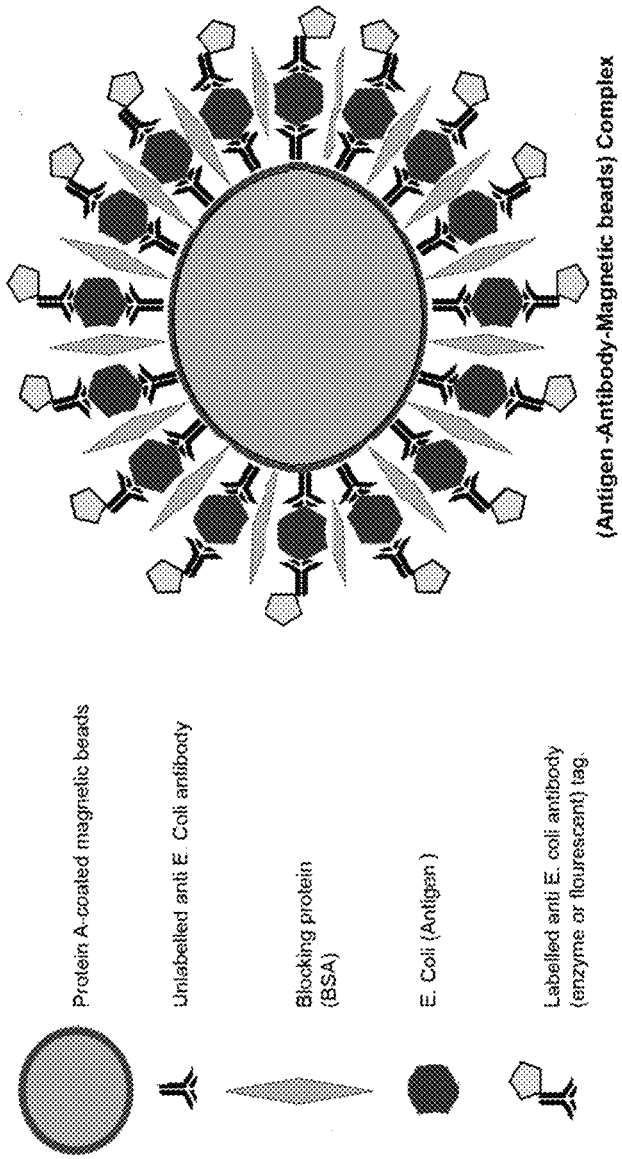
FIG. 1 is a schematic representation of immunomagnetic particles used for capturing and detecting target antigens in a food sample.
Figure 2:
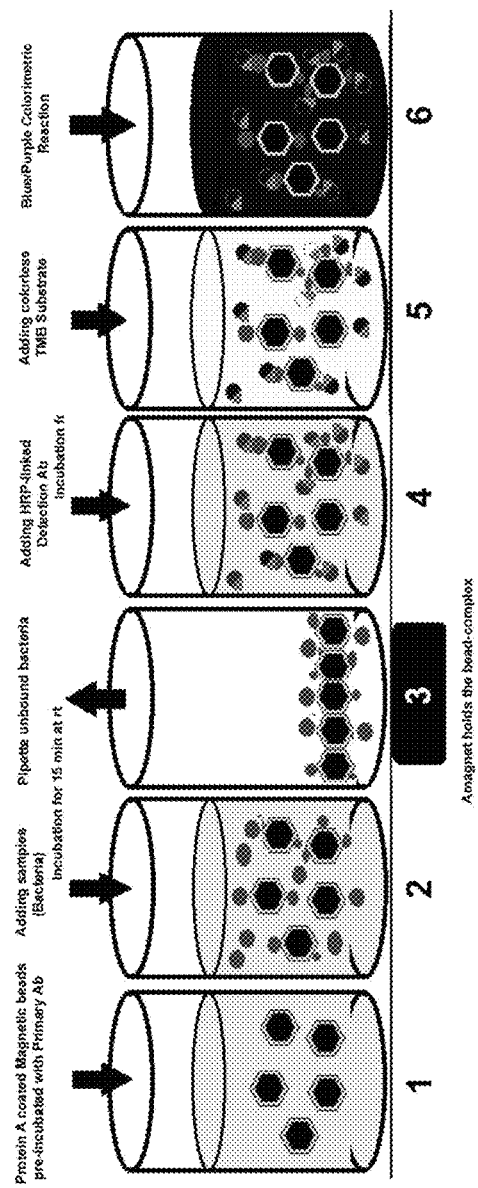
FIG. 2 is a schematic representation of the steps for capturing and detecting a food-borne pathogen.
Figure 3:
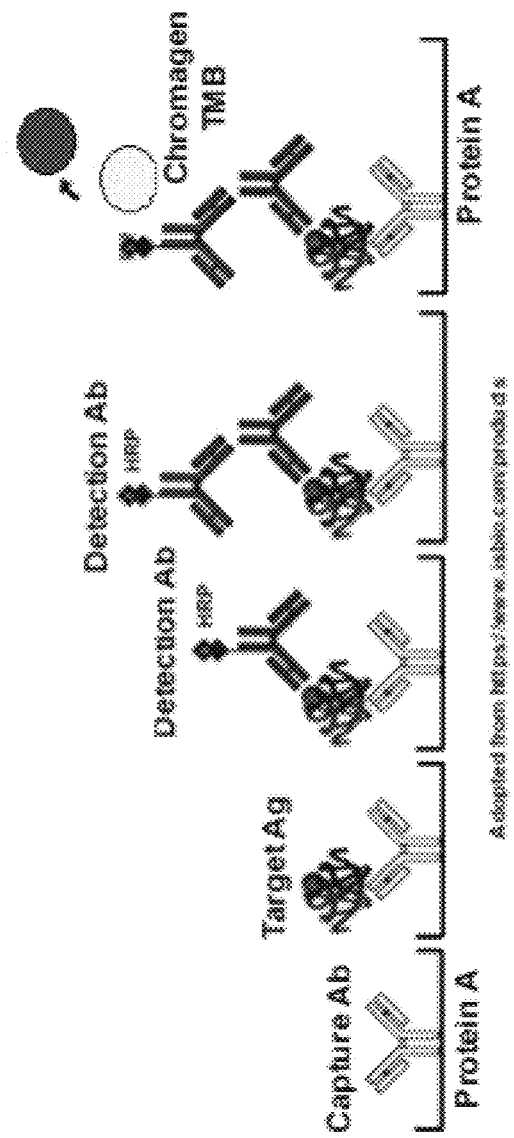
FIG. 3 is a schematic representation of the antibodies used for capturing and detecting target antigens.

To capture target particles/cells, the magnetic particles are coated with a particular ligand that binds to the target. The arrangement is shown schematically in FIGS. 1 and 2. In a first step, magnetic particles are coated with an immunoglobulin-binding protein (e.g., Protein A) that has pre-incubated with a primary or capture antibody that specifically detects an antigen if present in the sample and allowed to form a first complex, if present in the sample (see FIG. 1 and FIG. 2, panel 2). After a brief incubation period (e.g., 15 minutes; FIG. 2, panel 3) unbound sample is removed and a secondary or detector antibody linked to a detection moiety is added, which in this figure is horse radish peroxidase (HRP) (FIG. 2, panel 4). The assay is completed by identifying a detector moiety. When the HRP assay is used a colorless TMB substrate is added (FIG. 2, panel 5) after which a blue/purple color reaction occurs (FIG. 2, panel 6). This is also shown schematically in FIG. 3.

Immunoglobulin (Ig)-binding proteins (Protein-A, Protein-G) are suitable linker molecules that can be coated on the surface of the magnetic particles. These proteins specifically bind with immunoglobulin G (IgG) Abs and allow for easier and more precise purification of the pathogen. According to other embodiments, other linker molecules can also be used to bind antibody to the substrate.

In embodiments. OPS separation is used to combine the capture of the target antigen with an enzyme-based detection method to allow for a simultaneous colorimetric quantitation of the target antigen. Capture Ab are bound to a protein A-coated surface, which specifically captures the target antigen. The detection antibody linked to a horse radish peroxidase (HRP) enzyme applied to bind to the captured antigen. Addition of HRP chromogenic substrate TMB induces a colorimetric reaction, where the color intensity of the product is proportional to the amount of the detection Ab and thence to the amount of the captured target antigen. Thus, quantification of the resultant colorimetric reaction allows for quantification of the target antigen in the sample.

For OPS separation, the substrate used is magnetic. In certain embodiments, the substrate is magnetic particles. According to certain embodiments, the magnetic particles are substantially spherical. According to other embodiments, the magnetic particles have an average diameter from 20 nm to 165 µm. In certain embodiments, the magnetic particles have a diameter from 45 µm to 165 µm. In general, particles with a diameter near the smaller end of the range are used when more sensitive methods of detection are desired. Substantially spherical magnetic particles less than 200 µm in diameter are also referred to herein as micro-spherical magnetic (MSM) particles.

In certain embodiments, a non-magnetic substrate is used to bind the capture antibody. In these embodiments, the substrate can be a solid support that can be separated from an aqueous phase by filtering or centrifugation. In certain embodiments, the substrate is non-magnetic particles, or beads. These particles can be the same size and shape as the magnetic particles described herein.

The capture antibody described herein specifically binds to a desired antigen to be detected. The capture antibody can be either monoclonal or polyclonal. In certain embodiments, the capture antibody is an IgG antibody. The capture antibody is typically bound to the substrate according to the embodiments described herein. In other embodiments, the detector antibody is an antigen binding portion of an antibody as described herein.

The detector antibody described herein specifically binds to the same antigen as the corresponding capture antibody. In certain embodiments, the detector antibody specifically binds to this antigen at a site distinct from which the corresponding capture antibody binds. According to some embodiments, the detector antibody is not an IgG antibody and/or does not comprise an Fc region from an IgG antibody. In certain embodiments, the detector antibody is an IgY antibody or comprises the Fc region from an IgY antibody.

According to other embodiments, the detector antibody is selected from an IgA, IgD, IgE or IgM antibody. In other embodiments, the detector antibody is an antibody fragment as described herein.

In some embodiments, the detector antibody further comprises a detection moiety. The detection moiety is any moiety that allows detection and quantitation of the presence of the detector antibody. Detection moieties include horseradish peroxidase (HRP) and fluorescein isothiocyanate (FITC). Other examples of detection moieties include, but are not limited to, the following: radioisotopes or radionuclides (e.g., $^{3}$H, $^{14}$C, $^{35}$S, $^{90}$Y, $^{99}$Tc, $^{111}$In, $^{125}$I, $^{131}$I, $^{177}$Lu, $^{116}$Ho, or $^{153}$Sm); chromogens, fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates. Representative examples of labels commonly employed for immunoassays include moieties that produce light, e.g., acridinium compounds, and moieties that produce fluorescence, e.g., fluorescein. In this regard, the detection moiety itself may not be detectably labeled but may become detectable upon reaction with yet another moiety.

According to certain embodiments, the antigen that the capture and detector antibodies specifically bind to are expressed by microbes. According to certain embodiments, these microbes are food-borne pathogens. According to other embodiments, the microbes are bacteria, protists, fungi, viruses or other parasites. According to specific embodiments, the antigens are expressed on the surface of a food-borne pathogen.

Bacterial food-borne pathogens include certain strains of *E. coli*. In certain embodiments, the strain of *E. coli* is O157:H7. In another embodiment, the bacterial food-borne pathogen is a member of the *Salmonella* genus. In certain embodiments, the *Salmonella* species is *Salmonella enterica*. Other bacterial food-borne pathogens include *Campylobacter, Clostridium botulinum, Listeria monocytogenes, Staphylococcus aureus, Shigella* and *Vibrio vulnificus*.

Viral food borne-pathogens include norovirus, hepatitis A virus and rotovirus. Fungal food-borne pathogens include those that produce mycotoxins. In certain embodiments, the mycotoxins are aflatoxins. Fungal genera include *Aspergillus, Penicillium, Paecilomyces* and *Fusarium*. Protist food-borne pathogens include *Toxoplasma gondii, Cryptosporidium* spp. *Giardia intestinalis* and *Cyclospora cayetanensis*. Other parasites include round worms and tapeworms.

In certain embodiments, to prepare the sample, a sample of food or drink is incubated for a period of time under conditions that are conducive to growing the pathogen in question. For bacteria, a number of bacterial media can be used to enrich a sample for a pathogen to increase the chances of detection. In one embodiment, the medium is Tryptic Soy Broth (TSB). In certain embodiments, the TSB includes novobiocin. Other media includes LB broth, Terrific broth and M9 minimal medium. The sample is grown in media at a desired temperature for a period of time that allows sufficient growth of the microbe to allow its detection. In certain embodiments, the desired temperature is about 37° C. In other embodiments, the period of time is from 30 minutes to 24 hours. In other embodiments, the period of time is from 30 minutes to 1, 2, 3, 4, 5, 6, 7, 8, 9, 10, 11 or 12 hours.

The methods disclosed herein can be performed on devices or instruments known in the art and/or as disclosed herein. While the instrument and methods described herein are useful for detecting food-borne pathogens, any antigen could be detected at low concentration using this method.

The assay is coupled with a portable optical detection system to quantify the output of the detection moiety. In certain embodiments, the detection moiety provides a change in color intensity, for example, from the resultant HRP and TMB product as the HRP substrate produces a blue/purple color for optimal detection by the optical detection platform.

Also provided are kits that provide in one or more containers some or all of the reagents disclosed herein, e.g., capture and/or detector antibodies disclosed herein, magnetic particles, blocking agents (such as bovine serum albumin or BLOTTO™ mix), as well as reagents for detecting detection moieties of same. The kit may additionally include a sealed container. Optionally, an instruction manual for the use of the composition and the information about the composition are included in the kit.

In some embodiments, detection of antigens is with a commercially available detector, e.g., a Thorlab Model PDA1001 Newton, N.J., to provide a numeric value corresponding to color intensity, which correlates with the amount of the target bacteria in the test sample. The light source excitation wavelength and detector bandwidth range are chosen to match sample output wavelength and are aligned to collect output from multiple sample testing. Detection can alternatively be performed using the apparatus described herein. The optical instrument comprises at least one light source, at least one detector and a sample holder. The light source is capable of emitting a wavelength of light that is appropriate for exciting or detecting the detection moiety described herein. The detector is capable of detecting light that passes through or from a sample that is held in the sample holder.

Figure 4:
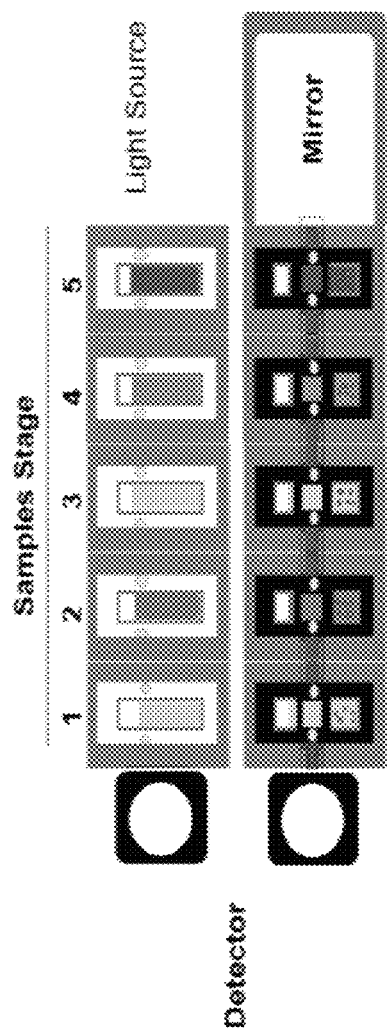
FIG. 4 is a schematic of the sample stage of an optical instrument.

In certain embodiments, the light source, detector and sample holder is arranged as shown in FIG. 4. The arrangement improves the focus of light from the light source and alignment in the detection chamber. The sample on this stage is subjected to two light sources, and the mirror is placed to allow maximum concentration of light that will be projected and collected by the detector. The automated stage will allow testing of 5 samples.

A schematic view of a photodetector system for use in detecting target antigens is shown in FIG. 10. An electrical signal output of the photodetector 102 in response to the detection of radiated sample energy 106 is amplified by an amplifier 112, analyzed by a level sensor 114, then processed by an appropriate signal processor 116 in order to detect the signal strength, corresponding to color intensity, of the respective sample, as a measure of antigen concentration bound by the detection platform. Information relating to which sample is being analyzed and the degree of color intensity may then be displayed on a display device 118 for operator review, and/or routed to a database 120 formed in a memory associated with the processor. Alternatively, or in addition thereto, the processor may provide a simplified display output, such as the sample under analysis is acceptable or is not acceptable. The display output may be configured according to the needs of and technical sophistication of the operator. In one embodiment, the processor is further adapted for storing data associated with each measurement, including a unique identification of each sample, and the color intensity measurement.

In certain other embodiments, the sample holder is motorized so that the samples are moved from a first position where they are placed in the optical instrument and a second position where they are exposed to light from the light source and adjacent the photodetector for detection of radiated illumination. Moving the samples to the second position limits the amount of ambient light that the samples are exposed to when the light source is emitting light. In other embodiments, the second position is located in a temperature controlled chamber in the optical instrument. According to certain embodiments, this temperature controlled chamber is kept at about 37° C. In certain embodiments, the sample holders can project a magnetic field to manipulate the magnetic particles that are held in the sample holders. In certain embodiments having a motorized sample holder, the sample holders are oriented in a substantially circular or continuous loop. Sample bearing tubes or cuvettes are introduced proximate to the sample holder pathway, then automatically aspirated and deposited into a cuvette prefilled with first antibody complex. Process steps according to the foregoing disclosure are then performed automatically, including incubation, separation and wash, and introduction of the second antibody complex prior to exposure to the light source or sources and detection of radiated energy by the photodetector, prior to automatic ejection of the sample cuvette in preparation for a new cuvette.

In certain embodiments, the optical instrument also includes one or more digital decoders and transducers for interpreting the results as well as a digital screen to present the results.

In other embodiments, the optical instrument also includes an incubation platform. In the incubation platform, samples can be kept at the appropriate temperature to enrich the population of microbe to be analyzed. In certain embodiments, the optical instrument provides power to maintain the samples at a given temperature. In one embodiment, this temperature is about 37° C. In other embodiments, the incubation platform is also provided a timing instrument to provide the length of time that samples are incubated.

Figure 5:
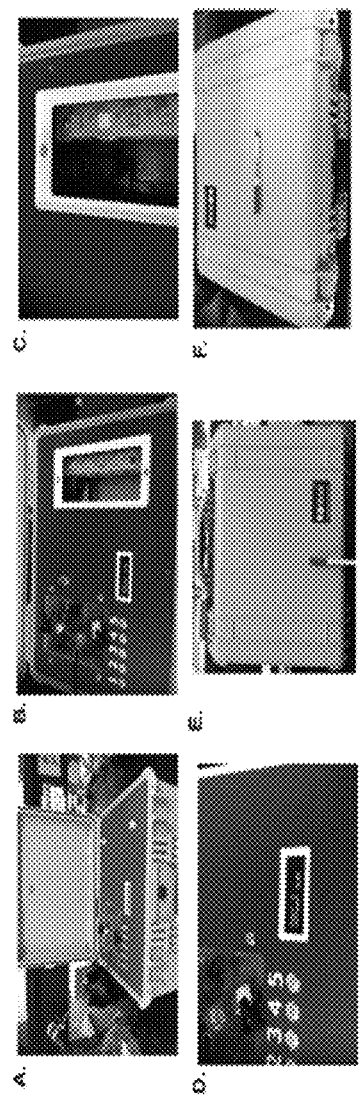
FIG. 5 shows photographs of an embodiment of the optical instrument described herein.

In one embodiment, the optical instrument is provided in FIG. 5. As shown in image F, the optical instrument can be provided in a portable casing. In certain embodiments, the casing is approximately the size of a suitcase. In certain embodiments, the casing is 0.5-1 m wide, by 0.5-1 m long, by 0.25-0.5 m deep. In certain embodiments, the optical instrument weighs between 5 and 10 kg.

Definitions

For convenience, certain terms used in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art. The terms used throughout this specification are defined as follows, unless otherwise limited in specific instances.

The articles "a," "an" and "the" are used to refer to one or to more than one (i.e., to at least one) of the grammatical object of the article.

The terms "comprise" "comprising" "including" "containing" "characterized by" and grammatical equivalents thereof are used in the inclusive, open sense, meaning that additional elements may be included. It is not intended to be construed as "consists of only."

As used herein, "consisting of" and grammatical equivalent thereof exclude any element, step or ingredient not specified in the claim.

As used herein, the term "about" or "approximately" usually means within 20%, more preferably within 10%, and most preferably still within 5% of a given value or range.

In some cases, a population of particles may be present. As used herein, the diameter of the particles is an average of a distribution in a particular population.

As used herein, one g/mole is equivalent to one "dalton" (i.e., dalton and g/mol are interchangeable when referring to the molecular weight of a polymer). "Kilodalton" as used herein refers to 1,000 daltons.

The term "antibody" refers to an immunoglobulin (Ig) molecule, which generally comprises of four polypeptide chains, two heavy (H) chains and two light (L) chains, or a functional fragment, mutant, variant, or derivative thereof, that retains the epitope binding features of an Ig molecule. Such fragment, mutant, variant, or derivative antibody formats are known in the art. In certain embodiments of a full-length antibody, each heavy chain is comprised of a heavy chain variable region (VH) and a heavy chain constant region (CH). The CH is comprised of three domains, CH1, CH2 and CH3. Each light chain is comprised of a light chain variable region (VL) and a light chain constant region (CL). The CL is comprised of a single CL domain. The VH and VL can be further subdivided into regions of hypervariability, termed complementarity determining regions (CDRs), interspersed with regions that are more conserved, termed framework regions (FRs). Generally, each VH and VL is composed of three CDRs and four FRs, arranged from amino-terminus to carboxy-terminus in the following order: FR1, CDR1, FR2, CDR2, FR3, CDR3, and FR4. Immunoglobulin molecules can be of any type (e.g., IgG, IgE, IgM, IgD, IgA and IgY), class (e.g., IgG1, IgG2, IgG3, IgG4, IgA1 and IgA2), or subclass. Variability exists in the endogenous antibodies between the species.

The term "specificity" refers to the ability of a binding protein to selectively bind an antigen.

The term, "affinity" refers the strength of the interaction between a binding protein and an antigen, and is determined by the sequence of the CDRs of the binding protein as well as by the nature of the binding protein and the antigen, such as their size, shape, and/or charge. Binding proteins may be selected for affinities that provide desired therapeutic endpoints while minimizing negative side-effects. Affinity may be measured using methods known to one skilled in the art (e.g., US 20090311253, incorporated by reference herein).

The term "control" refers to a composition known to not contain an analyte or test substance ("negative control") or to contain an analyte or test substance ("positive control"). A positive control can comprise a known concentration of an analyte or test substance. A "positive control" can be used to establish assay performance characteristics and is a useful indicator of the integrity of reagents (e.g., analytes or test substances). "Control," "positive control," and "calibrator" may also be used interchangeably herein to refer to a composition comprising a known concentration of an analyte or test substance.

The term "Fc region" defines the C-terminal region of an immunoglobulin heavy chain, which may be detached from the variable region of the immunoglobulin by papain digestion of an intact immunoglobulin. The Fc region may be a native sequence Fc region or a variant Fc region. The Fc region of an immunoglobulin generally comprises two constant domains, a CH2 domain and a CH3 domain, and optionally comprises a CH4 domain. Replacements of amino acid residues in the Fc portion to alter antibody effector function are known in the art (e.g., U.S. Pat. Nos. 5,648,260 and 5,624,821, incorporated herein by reference).

The term "antigen binding portion" or "antigen binding site" or "target binding site" of a binding protein means one or more fragments of a binding protein (e.g., an antibody or receptor), such as an immunoglobulin variable domain (e.g., VH or VL), that retain the ability to specifically bind to an antigen or target. The antigen binding portion of a binding protein can be performed by fragments of a full-length antibody, as well as bispecific, dual specific, or multi-specific formats; specifically binding to two or more antigens. Examples of binding fragments encompassed within the term "antigen binding portion" of an binding protein include (i) an Fab fragment, a monovalent fragment consisting of the VL, VH, CL and CH1 domains; (ii) an F(ab')2 fragment, a bivalent fragment comprising two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment, which comprises a single variable domain; and (vi) an isolated complementarity determining region (CDR). Furthermore, although the VH and VL of the Fv, which are encoded by separate genes, can be joined using recombinant methods by a synthetic linker that enables them to be made as a single protein chain in which the VH and VL regions pair to form monovalent molecules (known as single chain Fv (scFv). Such scFvs are also encompassed within the term "antigen binding portion" as are other forms of single chain antibodies, such as diabodies and "linear antibodies" comprising a pair of tandem Fv segments (VH-CH1-VH-CH1) which, together with complementary light chain polypeptides, form a pair of antigen binding sites. Not every amino acid of an antigen binding portion may bind to an antigen. For example, variable domains of an antibody comprise both complementarity determining regions (CDRs) and framework regions (FRs).

The term "CDR" means a complementarity determining region within an immunoglobulin variable region sequence. There are three CDRs in each of the variable regions of the heavy chain and the light chain, which are designated CDR1, CDR2 and CDR3, for each of the heavy and light chain variable regions. The term "CDR set" refers to a group of three CDRs that occur in a single variable region capable of binding the antigen. The exact boundaries of these CDRs have been defined differently according to different systems. The system described by Kabat (Kabat et al. (1971) Ann. NY Acad. Sci. 190:382-391; Kabat et al. (1987) Sequences of Proteins of Immunological Interest, Fourth Edition. US Govt Printing Off. No. 165-492; Kabat et al. (1991) Sequences of Proteins of Immunological Interest, Fifth Edition. NIH Publication No. 91-3242 incorporated herein by reference) not only provides an unambiguous residue numbering system applicable to any variable region of an antibody, but also provides precise residue boundaries defining the three CDRs. These CDRs may be referred to as Kabat CDRs. The terms "Kabat numbering", "Kabat definitions" and "Kabat labeling" are used interchangeably herein to refer to a system of numbering amino acid residues that are more variable (e.g., hypervariable) than other amino acid residues in the heavy and light chain variable regions of an antibody. Chothia and coworkers (Chothia and Lesk (1987) J. Mol. Biol. 196:901-917; Chothia et al. (1989) Nature 342:877-883) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chain regions, respectively. These regions may be referred to as Chothia CDRs, which have boundaries that overlap with Kabat CDRs. Other boundaries defining CDRs overlapping with the Kabat CDRs have been described by Padlan (1995) FASEB J. 9:133-139 and MacCallum (1996) J. Mol. Biol. 262(5):732-45). Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems.

The methods and apparatuses disclosed herein can be used on any substance for which microbial contamination is known or suspected. Thus, substances can include, liquids, e.g., water, milk, urine, blood, wine, honey, coffee, juices, solids, e.g., soil, beef, poultry, vegetables, or fruits, and gases e.g., air, water vapor, or oxygen.

In some embodiments, the pathogen is a food-borne pathogen. The food can be any food which is ingested by a host animal, e.g., a human or a mammal. The food can be obtained from an animal or plant source.

Any pathogen for which suitable capture and detection methods exist can be used in the methods and apparatuses of the invention. Therefore, pathogens include any eukaryotic or prokaryotic organism known to or suspected of causing disease in a host (typically a mammalian host such as a human).

In one embodiment, the pathogen is *E. coli* O157:H7. These bacteria are among the major causative agents for foodborne illnesses, which can cause diseases when present in food or water even at as low bacterial numbers as about 50 colony-forming unit (CFU), where the presence of a single CFU in any tested food sample denotes that at least a single living organism is present in the sample. Contaminated ground beef is the most common vehicle for *E. Coli* O157:H7 outbreaks. Beef products may become contaminated during slaughter, and the process of grinding beef may transfer pathogens from the surface of the meat to its interior. Therefore, if ground beef is incompletely cooked, the bacteria can survive. *E. coli* O157:H7 is an enterohemorrhagic strain capable of inducing diseases in humans through production of Shiga toxins. It has been reported to be associated with several outbreaks of hemorrhagic colitis, which can proceed to life-threatening hemolytic uremic syndrome (HUS), particularly in undiagnosed or untreated cases. The incidence rate of *E. coli* O157:H7 infection is estimated to be approximately 75,000 cases per year in the United States.

Another suitable pathogen for use in the methods and apparatuses of the invention is *Salmonella* spp., which are the most common cause of meat-associated food borne illness in the United States. Suitable strains include, e.g., *S. agona; S. anatum; S. enteritidis; S. havana; S. krefeld; S. lilee; S. melegredis; S. montevideo; S. munster: S. newport; S. saintpaul; S. schwarzengrund; S. tennessee; S. typhimurium* or *S. worthington*.

The methods and apparatuses disclosed herein can also be used to identify antigens of interest in biological fluids. Biological fluids include, e.g., whole blood, serum, plasma, spinal cord fluid, urine, and/or saliva. The antigen can be associated with a presumptive or known pathogen, or can be an endogenous antigen.

This invention also provides optical instrumentation specific for the optical platform. The optical platform allows specific, rapid, and sensitive detection of microbial contaminants in solid, liquid, and gaseous samples in comparison to the conventional standards of detection. This method will provide qualitative that can be quantified to determine concentration of contaminants.

This invention uses different synthesized binding agents which are coated on to micro sized particles. Those synthesized agents are specific to the target bacteria to detected. The tested sample is added to the detection platform which will generate a measurable optical change to be measured by the designed optical instrumentation.

If desired, the apparatus can be used as a benchtop instrument. Although the subject matter has been described in considerable detail with reference to certain embodiments thereof, other embodiments are possible. As such, the spirit and scope of the appended claims should not be limited to the description of the specific embodiments contained therein.

EXAMPLES

The disclosure will now be illustrated with working examples, which are intended to illustrate embodiments of the disclosure and not intended to add any limitations to the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, instruments and materials are described herein.

Materials and Methods

Micro-Spherical Magnetic Particles

Micro-spherical magnetic (MSM) particles were made with a spherical shape that provides a large surface to utilize for detection. The diameter range used was between 20 nm and 165 µm. The MSM particles surfaces were synthesized with protein A to on their surfaces.

Bacteria and Inoculum Preparation

The bacteria used in the study were *E. coli* O157:H7 (ATCC 700728) and *E. coli* O104:H4 (ATCC BAA-2326). *E. coli* O104:H4 was used as a negative control throughout the study. *E. coli* (EC) broth and mTSB+Novobiocin were used for culturing and selective culturing of the *E. coli* bacteria. Culture conditions were maintained with 8 h of incubation time at 37° C.

Immobilization of Antibody on the Protein-A Microspherical Magnetic (MSM) Particles

*E. coli* O157:H7 mouse monoclonal total IgG1 antibody (4 µg/µl) was immobilized on protein A-coated magnetic particles to serve as the capture-antibody specific to the epitopes O157 and H7 on the surface of whole *E. coli* O157:H7 bacteria in test samples.

The magnetic particles are supplied as a 10% particle suspension in phosphate-buffered saline (PBS) with 20% ethanol. 1 ml of 10% particle suspension contains 100 µl magnetic particles and the size of the magnetic particles ranges from 20 nm to 165 µm.

The magnetic particles volume was maintained at 10% (v/v) in the working solutions (10 ml sterile PBS, 5% BSA and 10% Magnetic particles) and the capture anti *E. coli* 0

157:H7 mouse IgG1 monoclonal antibody (4-5.5 µg/µl) in PBS pH 7.2 and 0.09% sodium azide and 5% w/v of Bovine Serum Albumin (BSA) purchased from (Sigma Life Science; Sigma-Aldrich, St. Louis, USA).

According to the product's specifications, 90% binding of the protein A particles was achieved after 60 min reaction with rabbit IgG at the concentration of (4 mg/ml) and the maximum binding capacity is accomplished at 6 mg human IgG/ml as determined by overloading tests. To saturate the binding capacity of the magnetic particles, the concentration of the anti E. coli O157:H7 capture-antibody was maintained as close as possible to the maximum binding limit of the magnetic particles and the working solution was incubated at 4° C. degrees for at least one hour prior to testing (stored at 4° C.).

Antibody (Ab) Immobilization

To validate the Ab immobilization process, FITC-labeled mouse anti-E. coli O157:H7 Mab was used in the immobilization procedure, as mentioned above. After immobilization, the Ab-immobilized MSM particles were subjected to spectrofluorometric emission scanning (at $\lambda Ex494$ nm) and fluorescence microscopic analysis. A standard graph, using the emission results of various known quantities of FITC-labeled AB, was used to find the maximum quantity of the Ab that became bound to the Protein-A MSM particles.

TRITC Labeling of Bacteria

To produce the desired number of cells, the culture was incubated for 8 hours; then 10 ml of the culture was centrifuged. The pellets were washed twice with PBS and resuspended in 1 ml of 2 mM TRITC in PBS. The content was mixed by pipetting and was then incubated for 10 min (4° C.) before the extra TRITC was centrifuged out. The resultant pellets were mixed with 0.5 ml of PBS and transferred to the Dye Removal Column for the removal of excess dye. Excess dye was removed per the manufacturer's instructions. The recovered TRITC-labeled bacteria were used for detection.

Capturing Antigen

In this step, 50 µl of FITC-labeled bacteria were added to the Ab-immobilized MSM particle mixture and mixed briefly (total reaction volume maintained at 250 µl using PBS). The mixture was incubated for 15 min at room temperature with gentle shaking. After incubation, the excess bacteria were washed out using PBS, while the MSM particles in the tube were retained with a magnet. After washing, the MSM particles were resuspended in PBS and plated on agar plates for verification of the bacterial binding and to provide the CFU bacterial count.

Quantification of Bacteria

To quantify bacteria in this test, a standard graph was prepared using 10 different dilutions of TRITC labeled bacteria. Various dilutions were subjected to an emission scan at $\lambda Ex541$ nm. The peak values of the emission scan were taken for standard graph preparation in addition to the bacterial concentrations of the respective dilutions. The bacterial concentration of each dilution was identified using colony forming unit (CFU) analysis.

Saturation Limit for Detection

To find the maximum bacterial population that would bind with 10 µl of Ab-immobilized MSM particles, saturation point analysis was performed. Different dilutions of TRITC-labeled bacteria were prepared and subjected to the antigen capturing process as described above. The emission values of each dilution were used in calculations with the standard curve to determine the bacterial concentrations.

CFU Analysis

Each diluted sample was subjected to CFU analysis to obtain bacterial concentrations. For serial dilutions, sterile deionized water was used; subsequently, the dilutions were plated on tryptic soy agar. Inoculated plates were incubated for 24 h at 37° C. After incubation, the plates were observed and the recorded values used in calculations for the number of CFU present in each dilution. To enumerate the mixed culture of both E. coli strains, dilutions were plated on MacConkey sorbitol agar.

Testing Beef and Spinach Samples

The methods and instrument were tested for their ability to detect bacterial contamination by E. coli O157:H7 (ATCC 700728). E. coli O157:H7 (ATCC 700728). and E. coli O104:H4 (ATCC BAA-2326) were obtained from American Type Culture Collection (ATCC, USA). The E. coli O104:H4 strain was used as a control to verify the specificity of the detection method.

Both growth broth or agar plates were used. E. coli (EC) broth and selective media of modified Tryptic Soy Broth with Novobiocin (mTSB+n) from (Fluka Analytical, USA) were used for culturing and selective enrichment of the bacteria in accordance with (FSIS, 2015) with incubation of cultures for 18 h at 37° C.

Preparation of the growth media is performed by weighing the required amount of the media as indicated by the manufacturer on the bottle for a given volume of 0.5-1 L and autoclaved at 121° C., 15 Psi for 15 min.

For preparation of agar plates for colony forming unit CFU enumeration, the media are prepared similar to the steps mentioned above and prior to autoclaving agar granules are added to melt with the media during autoclaving. Then immediately after autoclaving and before the agar solidify, the media with melted agar are poured in 60 mm or 100 mm petri dishes (purchased from Fisher Sci).

The agar plates were prepared under the hood preferably to avoid contamination of the plates. After complete solidification, the agar plates were stored at 4° C. until used in plating.

Binding of the E. coli O157:H7 to the magnetic particles-capture antibody complexes and cell count of bound bacteria was verified by a fluorescence assay and CFU enumeration. Serial dilutions of E. coli O157:H7 in PBS were prepared and plated on the selective mTSB+Novobiocin agar plates for CFU analysis to determine the correspondent bacterial concentrations. The detection limits and sensitivity of the immunomagnetic particles were determined by a series of serial dilutions, capture testing of various bacterial concentrations and concomitant selective plating and CFU counting.

Under a hood in aseptic conditions, 10 ml of the previously prepared sterile media is pipetted using sterile 10 ml serological tubes (Fisher Sci) and placed in sterile 15 ml tube. A 1 µl aliquot of growing bacteria is inoculated into the media and incubated at 37° C. to grow over night.

Immobilization of capture Anti E. coli O157:H7 antibody on Protein A-coated magnetic particles, Anti E. coli O157:H7 mouse monoclonal total IgG1 antibody (4 µg/µl) was performed on protein A-coated magnetic particles to serve as the capture-antibody specific to the epitopes O157 and H7 on the surface of whole E. coli O157:H7 bacteria in test samples.

Example 1. Microscopic Analysis

Fluorescence and light microscopic analysis were performed using an inverted microscope for possible green (FITC) and red (TRITC) fluorescence on the particles.

Captured images were processed using LAS AF6000 (2.5.0.6735) software. The presence of green fluorescence on the Protein-A MSM particles confirmed the immobilization of Ab (FITC), and red fluorescence confirmed the presence of whole cell E. coli O157:H7 AG (TRITC).

Figure 6:
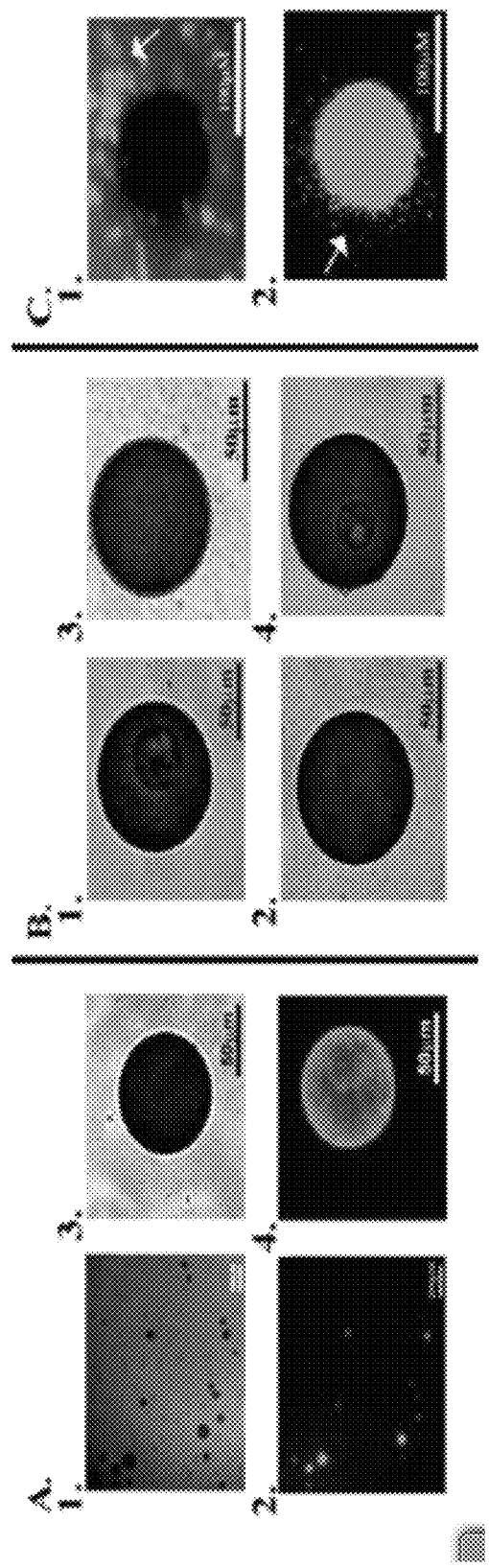
FIG. 6 shows bright field and fluorescent micrographs of *E. coli* O157:H7 binding to the MSM particle platform.

The results are shown in FIG. 6. Image A1 shows a low magnification (5×) broad view of a bright field microscopic image of the magnetic particles coated with FITC-conjugated capture antibody. Image A2 is the corresponding fluorescence microscopic image of FITC-labeled capture antibody-coated magnetic particles, while Image A3 and Image A4 are their respective high magnification (40×) counterparts. Image B shows bright field microscopy of magnetic particles (40×): Image B1 depicts Protein-A coated magnetic particles. Image B2 shows magnetic particles incubated with E. coli O157:H7 for 15 min in the absence of the capture antibody. Image B3 shows the addition of anti E. coli O157:H7 capture antibody. Image B4 depicts magnetic particles-capture antibody-E. coli O157:H7 complexes after washing with PBS. Image C shows fluorescence microscopy (40×) of magnetic particles with FITC-labelled E. coli O157:H7 (whole cells): Image C1 shows signal obtained in the absence of the capture anti E. coli O157:H7 antibody, while Image C2 shows signal obtained in the presence of the capture anti E. coli O157:H7 with post-capture washing of the unbound cells.

Example 2. Testing Bacterial Contamination Using a Meat Sample

To find the specificity and sensitivity of the test, combinations of different samples were prepared and tested with fluorescence microscopy. The scan was performed at an excitation wavelength of $\lambda Ex541$ nm. One set of samples was taken for microscopic analysis.

The instruments and methods were used to detect E. coli O157:H7 in food samples. Ground beef was bought from the local supermarket. In a Stomacher® bag, 25 g of meat was mixed with 50 ml of EC broth. This sample was inoculated with 132±2 CFU of E. coli O157:H7 (calculated by plating the inoculum) and homogenized using a Stomacher® 400 Circulator. In the same way, a second set of samples was prepared by inoculating both E. coli O157:H7 (132±2) and E. coli O104:H4 (131.5±1) cells as a mixed culture. The third set of samples was prepared only with E. coli O104:H4 (with 131.5±1 CFU) and used as a negative control. The same inoculation and homogenization were performed with raw ground beef samples as well. To identify whether the purchased ground beef was naturally infected with E. coli O157:H7, a set of raw samples were processed without inoculating E. coli O157:H7. After homogenization, the bag was incubated at 37° C. for 12 h. After incubation, the sample was briefly homogenized again with the Stomacher® machine. Then, 10 ml of solution was collected and centrifuged to retrieve the cell pellet. The pellet was then washed and suspended in 1 ml PBS. This prepared sample was mixed with the Protein-A MSM particles, described above. Positive control was maintained with a pure culture of E. coli O157:H7 inoculated (132±2 CFU) in the EC broth. Triplicates were maintained for all preparations in the study.

The specificity test showed accurate results for the samples containing bacteria with their respective Ab. The E. coli O157:H7 sample showed the highest fluorescence value with anti-E. coli O157:H7 pAb.

Figure 7:
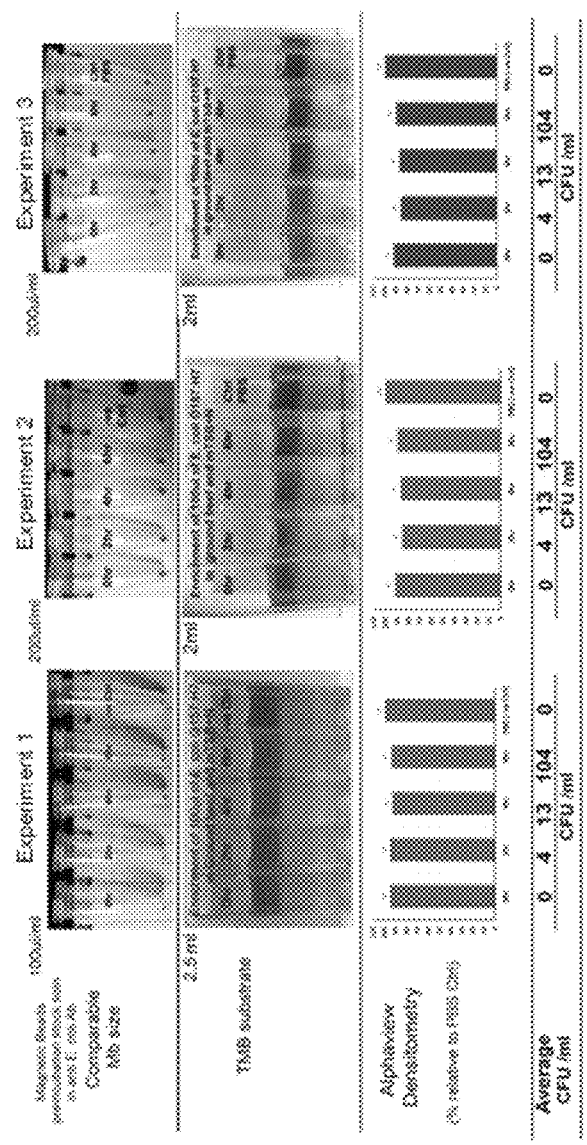
FIG. 7 shows densitometry of HRP action on TMB substrate in three different experiments.

The results are shown in FIG. 7. The figure shows results from replicated experiments (n=3) of ground beef samples enriched with E. coli O157:H7. Results were verified by conventional plating and counting of the resultant colony forming units (CFU) after the indicated periods of enrichment.

Significant fluorescence from the test of E. coli O157:H7—infected meat samples shows that the method is able to accurately capture the target bacteria from the infected food sample. There was no variation observed between the raw and inoculated meat samples. The control did not show any significant fluorescence. This means the locally purchased meat sample was not naturally infected with the E. coli O157:H7 pathogen. This food sample was enriched for 8 h; this time period was determined based on a separate experiment carried out using different time intervals to achieve a bacterial concentration that resulted in the maximum detection limit, as discussed previously. The bacteria infecting the meat (E. coli O157:H7) were able to grow in enrichment broth to a concentration of $8.55\pm0.21\times10^6$ CFU ml$^{-1}$. This concentration was achieved when the initially infected concentration of E. coli O157:H7 was only 2.6 CFU ml$^{-1}$. This showed that the enrichment process allows high sensitivity detection in food samples. This enrichment process also substantially reduced the time when compared to the methods for E. coli O157:H7 recommended by the US Food and Drug Administration (FDA) in their Bacteriological Analytical Manual (BAM).

Maximal capture of E. coli O157:H7 cells occurred with the polyclonal antibody, which also had the highest fluorescence value. In addition, the studies validated the accuracy of the instrument in testing contaminated meat samples.

100% accurate results were observed with all samples containing E. coli O157:H7 cells in these studies. Incubation of the infected meat sample was performed to mimic the natural contamination process, whereby the bacteria alive in the meat sample would begin to multiply in an enrichment media to reach a desirable bacterial concentration for detection. In addition, results obtained with the instrument were verified in conventional plating and counting of the resultant colony forming units (CFU) replicated experiments (n=3).

Example 3. Sample Testing Using Anti E. coli O157:H7—Chicken IgY

100 μl of the magnetic particles-capture antibody working solution (equivalent to 10 μl of magnetic particles) was loaded into 1.5 ml Eppendorf tube for each sample tested. For every experiment an Eppendorf tube was set as a negative control to test a sterile PBS sample or a non-inoculated sample.

Magnetic particles and samples were incubated at room temperature for 15 minutes with shaking at 40 RPM to allow gentle but thorough mixing of samples and magnetic particles for maximum binding. After the 15 minutes incubation, the magnetic particle complex formed by the mixing was washed twice in 0.5 ml sterile PBS with gentle mixing at 40 RPM at room temperature to wash away unbound bacteria.

Following the washing steps, the magnetic particles-bacteria were immersed in 600 μl of sterile PBS and mixed gently by pipetting. Then 300 μl (half of the magnetic particle complex) was plated and spread on the agar plates for simultaneous verification of the CFU count of the bound bacterial cells for later comparison.

The efficiency of the magnetic particles in capturing bacteria was determined by comparison of the CFU of bound bacteria and CFU of raw tested samples. Efficiency was usually 30-50% (data not shown). If serial dilutions were tested or high bacterial concentration was expected from undiluted samples or due to extended periods of enrichment, then serial dilutions were made of the sample of interest to facilitate countable CFUs and cell count of the original samples. Magnetic particle-sample complexes were incubated with the enzyme-linked detection anti E. coli O157-Horseradish Peroxidase (HRP)-linked mouse Mab (1 mg/ml).

The immunomagnetic particle complexes were then incubated in blocking buffer 5% BSA (Sigma Life Science; Sigma-Aldrich, St. Louis, USA) in PBS or 5% nonfat dry milk in PBS.

HRP-linked anti E. coli O157:H7 chicken IgY antibodies were purified to be used as detection Ab. The antibodies were produced by immunization of chicken embryo to elicit the formation of anti E. coli O157:H7 IgY antibody from the yolk sac, which was purified and then conjugated with HRP enzyme to be used as a detection antibody in the platform. Therefore, while the detection protocol and steps are the same as for mammalian-based antibody detection, the advantage of this approach is that HRP-linked chicken IgY antibodies will not bind to protein A.

After incubation with test samples, the immunomagnetic particles complexes were incubated with the enzyme-linked detection anti E. coli O157—chicken IgY (customized Ab linked to Horseradish Peroxidase (HRP) at 2 mg/ml). The anti E. coli O157:H7 Chicken IgY detection antibody working solution was prepared in a 15 ml sterile tube containing sterile PBS, 5% BSA and 50 μl-150 μl of IgY i.e., 100-300 μg of the antibody, which is tailored on the basis of the intensity of the resultant color intensity and consequently times of washing and volume of HRP-chromogenic substrate 3,3',5,5'-tetramethylbenzidine (TMB) substrate used as well as the time of reaction. The lowest effective volume of detection antibody was recommended, in contrast to the capture antibody, where the highest concentration possible was preferable.

In addition to the use of high concentrations of the capture antibody to saturate the magnetic particles binding capacity, 5% BSA or 5% Nonfat dry milk blocking buffers were used to reduce the potential nonspecific direct binding of the detection antibody to the magnetic particles and consequently the inadvertent false positive results.

Following the incubation with the detection antibody, the immunomagnetic particle-complexes were washed with PBS to remove the excess unbound detection antibody. In contrast to the capture antibody that could be recollected prior to the addition of sample the detection antibody was not recollected and was decanted.

After the addition of the detection IgY antibody (300 μl of the working solution to each sample) the samples are incubated according to the protocol for 15 minutes at room temperature with gentle shaking at 40 RPM.

The detection antibody was aspirated and decanted while the magnetic particles were firmly held to the side of the tube using a magnetic field. The magnetic particles complexes were immersed in 0.5-1 ml of sterile PBS with shaking at room temperature for 5 minutes, 2-3 times. The washout was decanted while the magnetic particles were held by the magnet. A washing tube was used as an internal control, which receives only the detection antibody and was washed similarly and tested by adding the enzyme substrate to check for color formation i.e., remainder of the detection antibody to control for adequacy of washing.

The HRP reagent used was HRP-chromogenic substrate 3,3',5,5'-tetramethylbenzidine (TMB). Pierce 1-Step Ultra TMB was added and the tube contents with 1 ml of TMB were then transferred to a counterpart clean and dry transparent cuvettes to be measured and results recorded.

Figure 8:
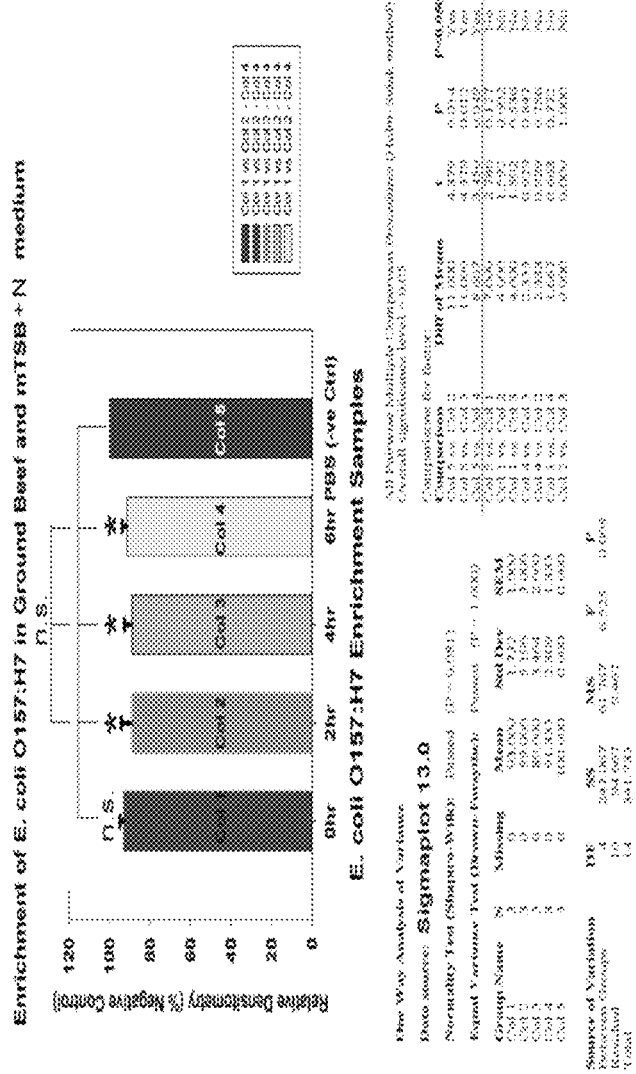
FIG. 8 shows densitometry of HRP action on TMB substrate following enrichment of *E. coli* O:157:H7 in ground beef and in mTSB+ medium.

The enrichment of E. coli O:157:H7 in ground beef and mTSB+medium is shown in FIG. 8. Shown is the Relative Densitometry (% Negative Control) at 0 hr (Col 1), 2 h (Col 2), 4 hr (Col 3), 6 hr (Col 4) or PBS (Col 5; negative control). For each time point, the results were obtained using the platform for capture and detection in triplicate of ground beef samples inoculated with E. coli O157:H7 non-virulent mutant variant.

Using a SigmaPlot version 13.0 statistical software, an ANOVA test was performed to calculate the statistical significance of the differences between the means of the color intensity among the various samples. The differences in the mean values among the different samples were greater than would be expected by mere chance (p<0.01). Moreover, Holm-Sidak ANOVA post-hoc testing shows that the mean values of the samples inoculated with the target bacteria are in particular significantly different from the negative control (PBS) as well as ground beef samples at 0 hrs of enrichment.

Figure 9:
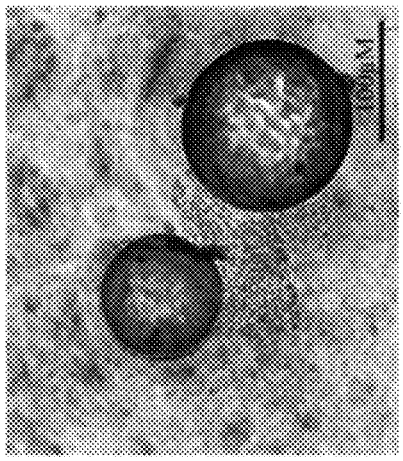
FIG. 9 shows micrographs showing the blue/purple stain of TMB due to the action of HRP and localization of the stain around the spherical magnetic particle platform where target *E. coli* O157:H7 is captured.
Figure 9:
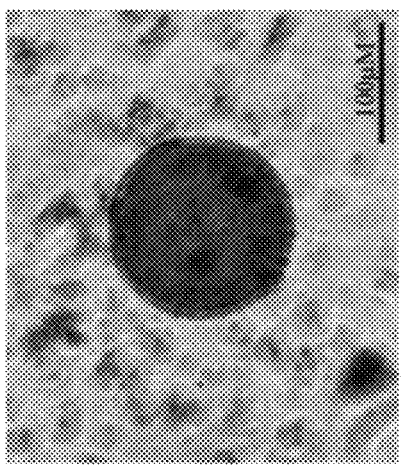

FIG. 9 shows the blue/purple stain of TMB due to the action of HRP and localization of the stain around the spherical magnetic particle platform where target E. coli O157:H7 is captured. Image A contains magnetic particle platform+E. coli O157:H7+ HRP-capture antibodies (Ab) (IgY)+TMB. In this sample, an IgG linker Ab is not present to bind to protein A, which is coated on the magnetic particle platform. After the addition of E coil O157:H7 no binding will take place to the platform. Then after the wash of that step, the pathogens will wash off. When HRP-capture antibodies (Ab) (IgY) are added and washed, only the magnetic particle platform remained when TMB was added. There was no reaction as shown. Image B shows the magnetic particle platform+IgG (Ab) bound to protein A. E. coli O157:H7 is added to the matrix then incubated for 15 minutes then washed. Under these conditions the magnetic particle platform coated with protein A and IgG had E. coli O157:H7 bound to primary IgG (Ab). After this HRP-capture Antibodies (Ab) (IgY) were added and washed. This step lead to the binding of HRP-secondary Antibodies (Ab) (IgY) to E. coli O157:H7, which is also bound to the primary IgG (Ab). Then TMB is added, which reacts with HRP to produce a purple/blue color.

This figure shows that the blue/purple stain of TMB is due to the action of HRP and localization of the stain around the magnetic particles where target E. coli is captured.

Example 4. Testing of Ground Beef Sample Processed for Prolonged Enrichment 3.6±0.1 g of ground beef, 90-100% lean were weighed under septic conditions and either placed in a sterile Stomacher® bag or sterile 50 ml tube and submersed in 10 ml of mTSB+n. Cultures were inoculated with 0.5 ml SD-8 E. coli O157:H7 and incubated at 37° C. for the following time points: 0, 2, 4, 6, 12, 18, 24.48 hours. An uninoculated negative control was also provided. 1 ml of enriched broth was spun for 10 seconds to precipitate meat debris and fat, and 0.5 ml was collected as sample from the supernatant and tested with 200 μl preincubated magnetic particles+ IgG anti E. coli Ab for 20 min followed by washing two times for 5 min each in 1 ml PBS with constant shaking. Magnetic particle complexes were resuspended in 1 ml sterile PBS. Half of the suspension, 0.5 ml, was plated for CFU count while 0.5 ml was kept in the 1.5 ml tube. The magnetic particles were retained with a magnet and excess PBS was aspirated. The magnetic particle complex were then incubated with 0.5 ml of IgY HRP detection Ab for 20 min with shaking at room temperature followed by washing three times in 1 ml PBS for 5 minutes each with shaking. 1 ml of TMB substrate was added. Color was measured after 10-20 minutes.

What is claimed:

1. A method of detecting an antigen, the method comprising:
   mixing a solution comprising a sample suspected of containing the antigen and a capture antibody, which specifically binds to the antigen, in conditions sufficient to form a first complex between the antigen and the capture antibody, wherein the capture antibody is linked to an immobilization moiety by a protein that binds to the Fc region of an IgG antibody;
   separating unbound capture antibody from the first complex;
   adding a detector antibody linked to a detection moiety, which specifically binds at a distinct site on the antigen, under conditions sufficient to form a second complex between the first complex and the detector antibody, wherein the detector antibody comprises an IgY Fc region and the detection moiety is a fluorescent dye;
   separating unbound detector antibody from the second complex; and
   detecting the fluorescent dye on the second complex by fluorescence spectroscopy, thereby detecting the antigen,
   wherein the antigen is located on the surface of a microorganism and the microorganism is present at a concentration between one viable microorganism per 125 g of the sample and one viable microorganism per 425 g of the sample.

2. The method of claim 1, wherein the antigen is present on a food-borne pathogen.

3. The method of claim 2, wherein the food-borne pathogen is a bacterium.

4. The method of claim 3, wherein the bacterium is an *E. coli* or *Salmonella* spp.

5. The method of claim 4, wherein the *E. coli* is an *E. coli* O157:H7 strain.

6. The method of claim 1, wherein the capture antibody is an IgG antibody.

7. The method of claim 1, wherein the immobilization moiety is a magnetic particle.

8. The method of claim 7, wherein the magnetic particle has an average diameter of between 20 nm and 165 µm.

9. The method of claim 8, wherein the magnetic particle is coated with a protein that binds the Fc region of the IgG antibody.

10. The method of claim 9, wherein the protein is Protein A.

11. The method of claim 1, further comprising culturing the solution comprising the sample suspected of containing the antigen under conditions sufficient to allow for growth of the microorganism prior to mixing the solution with the capture antibody.

12. The method of claim 11, wherein the microorganism is a food-borne pathogen.

13. The method of claim 12, wherein the food-borne pathogen is a bacterium.

14. The method of claim 13, wherein the bacterium is an *E. coli* O157:H7 strain.

15. The method of claim 1, wherein the detector antibody is an IgY antibody.

16. The method of claim 15, wherein the IgY antibody is a chicken IgY antibody.

17. The method of claim 1, wherein the fluorescent dye is selected from the group consisting of fluorescein, fluorescein isothiocyanate (FITC), rhodamine, lanthanide, and a phosphor.

18. The method of claim 1, wherein the fluorescent dye has an excitation wavelength between 450 nm to 700 nm.

19. The method of claim 1, wherein the detection is qualitative.

20. The method of claim 1, wherein the detection is quantitative.

* * * * *